(12) United States Patent
Schankereli et al.

(10) Patent No.: US 7,871,639 B2
(45) Date of Patent: *Jan. 18, 2011

(54) BIOCOMPATIBLE PHASE INVERTABLE PROTEINACEOUS COMPOSITIONS AND METHODS FOR MAKING AND USING THE SAME

(75) Inventors: Kemal Schankereli, Stillwater, MN (US); Ronald Dieck, Palo Alto, CA (US)

(73) Assignee: Matrix Medical, LLC, Palo Alto, CA (US)

( * ) Notice: Subject to any disclaimer, the term of this patent is extended or adjusted under 35 U.S.C. 154(b) by 251 days.

This patent is subject to a terminal disclaimer.

(21) Appl. No.: 11/877,396

(22) Filed: Oct. 23, 2007

(65) Prior Publication Data

US 2008/0096977 A1    Apr. 24, 2008

Related U.S. Application Data

(63) Continuation of application No. 10/635,847, filed on Aug. 5, 2003, now Pat. No. 7,303,757, which is a continuation-in-part of application No. 10/243,482, filed on Sep. 13, 2002, now abandoned.

(60) Provisional application No. 60/401,282, filed on Aug. 6, 2002.

(51) Int. Cl.
*A61F 2/02* (2006.01)
*A61F 2/06* (2006.01)
*A61M 5/00* (2006.01)

(52) U.S. Cl. ............... 424/423; 424/400; 424/422; 604/264; 623/1.1

(58) Field of Classification Search ............... 424/422, 424/423, 400; 604/264; 623/1.1
See application file for complete search history.

(56) References Cited

U.S. PATENT DOCUMENTS

| 3,438,374 A | 4/1969 | Falb et al. |
| 3,559,652 A | 2/1971 | Banitt et al. |
| 5,092,841 A | 3/1992 | Spears |

(Continued)

FOREIGN PATENT DOCUMENTS

CA    2425935    10/2002

(Continued)

OTHER PUBLICATIONS

Prusiner, Stanley, "Prion Diseases and the BSE Crisis," Sciences, vol. 278, 1997, p. 245-251.

(Continued)

*Primary Examiner*—Gollamudi S Kishore
(74) *Attorney, Agent, or Firm*—Bret E. Field; Bozicevic, Field & Francis, LLP

(57) ABSTRACT

Biocompatible phase invertable proteinaceous compositions and methods for making and using the same are provided. The subject phase invertable compositions are prepared by combining a proteinaceous substrate and a cross-linker. The proteinaceous substrate includes one or more proteins and an adhesion modifier, and may also include one or more of: a plasticizer, a carbohydrate, or other modification agent. In certain embodiments, the cross-linker is a heat-treated dialdehyde, e.g., heat-treated glutaraldehyde. Also provided are kits for use in preparing the subject compositions. The subject compositions, kits and systems find use in a variety of different applications.

21 Claims, 2 Drawing Sheets

U.S. PATENT DOCUMENTS

| | | |
|---|---|---|
| 5,219,895 A | 6/1993 | Kelman et al. |
| 5,292,362 A | 3/1994 | Bass et al. |
| 5,385,606 A | 1/1995 | Kowanko |
| 5,583,114 A | 12/1996 | Barrows et al. |
| 5,817,303 A | 10/1998 | Stedronsky et al. |
| 5,843,156 A | 12/1998 | Slepian et al. |
| 6,162,241 A | 12/2000 | Coury et al. |
| 6,290,729 B1 | 9/2001 | Slepian et al. |
| 6,299,631 B1 | 10/2001 | Shalaby |
| 6,302,898 B1 | 10/2001 | Edwards et al. |
| 6,310,036 B1 | 10/2001 | Browdie |
| 6,329,337 B1 | 12/2001 | Morita et al. |
| 6,371,975 B2 | 4/2002 | Cruise et al. |
| 6,372,229 B1 | 4/2002 | Ollerenshaw et al. |
| 6,423,333 B1 | 7/2002 | Stedronsky et al. |
| 6,458,147 B1 | 10/2002 | Cruise et al. |
| 6,475,182 B1 | 11/2002 | Hnojewyj et al. |
| 6,547,806 B1 | 4/2003 | Ding |
| 6,554,851 B1 | 4/2003 | Palasis et al. |
| 6,561,970 B1 * | 5/2003 | Carpentier et al. ............ 600/36 |
| 7,303,757 B2 * | 12/2007 | Schankereli et al. ........ 424/423 |
| 2002/0015724 A1 | 2/2002 | Yang et al. |
| 2002/0022588 A1 | 2/2002 | Wilkie et al. |
| 2002/0133193 A1 | 9/2002 | Ginn et al. |
| 2002/0173770 A1 | 11/2002 | Flory et al. |
| 2002/0183244 A1 | 12/2002 | Ollerenshaw et al. |
| 2002/0198490 A1 | 12/2002 | Wirt et al. |
| 2003/0032143 A1 | 2/2003 | Neff et al. |
| 2003/0125813 A1 | 7/2003 | Carpentier et al. |
| 2004/0030405 A1 | 2/2004 | Carpentier et al. |

FOREIGN PATENT DOCUMENTS

| | | |
|---|---|---|
| EP | 1043034 A1 | 10/2000 |
| WO | 97/22372 A1 | 6/1997 |
| WO | 01/45761 A1 | 6/2001 |

OTHER PUBLICATIONS

Merck Index, 1983, pp. 641-642.

* cited by examiner

BIOCOMPATIBLE PHASE INVERTABLE PROTEINACEOUS COMPOSITIONS AND METHODS FOR MAKING AND USING THE SAME

CROSS REFERENCE TO RELATED APPLICATIONS

The present application is a continuation application of application Ser. No. 10/635,847 filed on Aug. 5, 2003 and now issued as U.S. Pat. No. 7,303,757; which application is a continuation-in-part application of U.S. application Ser. No. 10/243,482 filed on Sep. 13, 2002, now abandoned the disclosure of which is herein incorporated by reference; and also claims priority Pursuant to 35 U.S.C. §119 (e) to the filing date of U.S. Provisional Application Ser. No. 60/401,282, filed on Aug. 6, 2002, the disclosure of which is herein incorporated by reference.

INTRODUCTION

1. Field of the Invention

The field of this biocompatible compositions, including biocompatible sealant compositions.

2. Background of the Invention

Recently, a number of sealant compositions have become available to control fluid leakage at a surgical site, as well as for other applications. However, currently available sealant compositions may suffer from serious limitations with regards to the field in which they can be used, as well as their biocompatibility and their physical properties. Side effects, such as inflammation, acute fibrous formation at the wound site, toxicity, inability to be used in a bloody field, poor physical properties of the sealant, and poor adhesion to the surgical site, may have a serious impact on the patient and resultantly may play a significant role in the long term efficacy of the repair. Further, useful sealants have properties that can render them more effective for surgical application. Characteristics, such as the ability to be localized to a specific location, adequately long or short polymerization times, and adequate in vivo resorption characteristics, are vital to a successful completion of the sealing procedure.

As such, there is a continued need for the development of new biocompatible compositions for use as sealants, as well as for use in other applications.

SUMMARY OF THE INVENTION

Biocompatible phase invertable proteinaceous compositions and methods for making and using the same are provided. The subject phase invertable compositions are prepared by combining a proteinaceous substrate and a cross-linker. The proteinaceous substrate includes one or more proteins and, at least in many embodiments, an adhesion modifier, and may also include one or more of: a plasticizer, a carbohydrate, or other modification agent. In certain embodiments, the cross-linker is a heat-treated dialdehyde, e.g., heat-treated glutaraldehyde. Also provided are kits for use in preparing the subject compositions. The subject compositions, kits and systems find use in a variety of different applications.

DESCRIPTION OF THE SPECIFIC EMBODIMENTS

Figure 1A:
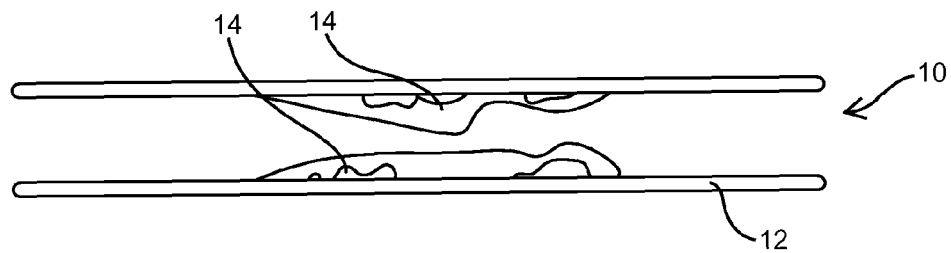
FIGS. 1A to 1E illustrate the in situ production of a biocomposite stent according to a representative embodiments of the subject invention.

Biocompatible phase invertable proteinaceous compositions and methods for making and using the same are provided. The subject phase invertable compositions are prepared by combining a proteinaceous substrate and a cross-linker. The proteinaceous substrate includes one or more proteins and, at least in many embodiments, an adhesion modifier, and may also include one or more of: a plasticizer, a carbohydrate, or other modification agent. In certain embodiments, the cross-linker is a heat-treated dialdehyde, e.g., heat-treated glutaraldehyde. Also provided are kits for use in preparing the subject compositions. The subject compositions, kits and systems find use in a variety of different applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

In further describing the subject invention, the subject phase invertable compositions are described first in greater detail, followed by a review of representative applications in which the compositions find use, as well as a review of kits and systems that find use in making or using the subject phase invertable compositions.

Biocompatible Phase Invertable Proteinaceous Composition

As summarized above, the subject invention provides a biocompatible phase invertable proteinaceous composition that, over time, undergoes a phase inversion from a first, fluid state to a second, solid state. The subject phase invertible compositions are characterized by being capable of bonding tissue in both wet (e.g., blood) and dry environments, where adhesion of the composition to the tissue is exceptionally strong. A further feature of the subject compositions is that they are well tolerated and do not elicit a substantial inflammatory response, if any inflammatory response.

The subject phase invertable proteinaceous compositions are prepared by combining or mixing a proteinaceous substrate with a crosslinker. Each of these precursor components or compositions is now reviewed separately in greater detail.

Proteinaceous Substrate

The proteinaceous substrate from which the subject phase invertable compositions are prepared is generally a fluid composition, e.g., an aqueous composition, that is made up of at least a proteinaceous component and, at least in many embodiments, an adhesion modifier, where the substrate may include one or more additional components, including, but not limited to: a plasticizer; a carbohydrate; and the like.

Proteinaceous Component

The proteinaceous component of the substrate is made up of one or more distinct proteins. The proteins of this component may be either synthetic or naturally occurring proteins, where the proteins may be obtained/prepared using any convenient protocol, e.g., purification from naturally occurring sources, recombinant production, synthetic production, and the like, where in certain embodiments the proteins are obtained from naturally occurring, e.g., bovine or human, sources. Specific proteins of interest include, but are not limited to: albumins, collagens, elastins, fibrins, and the like.

The amount of protein in the substrate composition may vary, where the specific selection of concentration is dependent on the desired application and product parameters desired therefore, such as tenacity, hardness, elasticity, resorption characteristics and platelet aggregation effects. In certain embodiments, the total protein total concentration in the substrate compositions ranges from about 1 to 75% (w/w), such as 1-50% (w/w), including 5 to 40% (w/w).

In certain embodiments, the primary protein of the substrate composition of this embodiment is albumin, where the albumin may be a naturally occurring albumin, e.g., human albumin, bovine albumin, etc., or a variant thereof. As is known in the art, the albumin may be purchased in powdered form and then solubilized into an aqueous suspension, or alternately, may be purchased in aqueous form. Purified albumin may derived from any one of a number of different sources including, bovine, ovine, equine, human, or avian in accordance to well known methods (ref.: Cohn et. Al, J. Amer. Chem. Soc. 69:1753) or may be purchased in purified form from a supplier, such as Aldrich Chemical (St. Louis, Mo.), in lyophilized or aqueous form. The albumin may be derivatized to act as a carrier for drugs, such as heparin sulfate, growth factors, antibiotics, or may be modified in an effort to moderate viscosity, or hydrophilicity. Derivitization using acylating agents, such as, but not limited to, succinic anhydride, and lauryl chlorides, are useful for the production of binding sites for the addition of useful molecules. In these embodiments where the proteinaceous component includes albumin, the albumin may be present in concentrations ranging from about 10 to about 50% (w/w), such as from about 30 to about 40% (w/w).

In certain embodiments, the proteinaceous component also includes a collagen, e.g., a naturally occurring collagen (human, bovine) or synthetic variant thereof. In accordance with the invention, the collagen may be in dry or aqueous forms when mixed with the albumin. Collagen may be derivatized to increase it utility. Acylating agents, such as anhydrides or acid chlorides, have been found to produce useful sites for binding of molecules such as growth factors, and antibiotics. When present, the collagen sometimes ranges from about 1 to about 20% (w/w), including from about 1 to about 10% (w/w), such as from about 1 to about 4% (w/w), including from about 2 to 4% (w/w).

The subject proteinaceous component, as described above, may or may not include one or more active agents, e.g., drugs, present in it, as desired. When present, the agent(s) may be bound to the polymers, as desired.

Adhesion Modifier

Also present in at least many of the embodiments of the substrate is one or more adhesion modifiers or tacking agents. Adhesion modifiers (also referred to herein as tacking agents) improve the adhesiveness of the sealant to the biological surface. In many embodiments, the adhesion modifiers are polymeric compounds having charged functionalities, e.g., amines, etc. Whereas numerous adhesion modifiers may be used, one of particular applicability is polyethyleneimine (PEI). PEI is a long chain branched, alkyl polymer containing primary, secondary and tertiary amines. The presence of these highly ionic groups results in significant attachment through ionic interactions with the underlying surface. In addition, the presence of PEI in the substrate significantly enhances the presence of amine terminals suitable to produce crosslinks with the crosslinking agent. Additional adhesion modifiers of interest include, but are not limited to: gelatin, carboxymethylcellulose, butylhydroxytoluene, etc.

In certain embodiments of the invention, adhesion modifiers are used to modify adhesion to the biological substrate while simultaneously creating a procoagulant. In certain embodiments, the adhesion modifiers are present in concentrations of from about 0.1 to about 10% (w/w), such as from about 0.5 to about 4% (w/w).

Optional Components

The above described substrate component of the subject compositions may, in certain embodiments, include one or more optional components that modify the properties of the phase invertable composition produced from the substrate and crosslinker. Representative optional components of interest are now discussed in greater detail below.

Plasticizing Agents

In accordance to the invention, a plasticizing agent may be present in the substrate. The plasticizing agent provides a number of functions, including wetting of a surface, or alternately, increasing the elastic modulus of the material, or further still, aiding in the mixing and application of the material. Numerous plasticizing agents exist, including fatty acids, e.g., oleic acid, palmitic acid, etc., dioctylphtalate, phospholipids, and phosphatidic acid. Because plasticizers are typically water insoluble organic substances and are not readily miscible with water, it is sometimes advantageous to modify their miscibility with water, by pre-mixing the appropriate plasticizer with an alcohol to reduce the surface tension associated with the solution. To this end, any alcohol may be used. In one representative embodiment of this invention, oleic acid is mixed with ethanol to form a 50% (w/w) solution and this solution then is used to plasticize the proteinaceous substrate during the formulation process. Whereas the type and concentration of the plasticizing agent is dependent upon the application, in certain embodiments the final concentration of the plasticizing agent is from about 0.01 to 10% (w/w), including from about 2 to about 4% (w/w). Other plasticizing agents of interest include, but are not limited to: polyethylene glycol, glycerine, butylhydroxytoluene, etc.

Carbohydrate Procoagulant

In certain embodiments, the substrates include a carbohydrate procoagulant. Chitosan and derivates of chitosan are potent coagulators of blood and, therefore, are beneficial in formulating sealant materials capable of sealing vascular injuries. While virtually all chitin materials have been demonstrated to have some procoagulant activity, in accordance to the invention, the use of acetylated chitin is preferable as an additive for the formulation of sealant intended for blood control. Acetylation of the molecule can be achieved in a number of different ways, but one common method is the treatment of chitosan/acetic acid mixtures with acid anhydrides, such as succinic. This reaction is readily carried out at room temperature. In accordance to the invention, gels created in this manner combined with proteinaceous substrates and crosslinked in situ are beneficial for the creation of a biocomposite structural member. In accordance with the teachings of this invention the carbohydrate component, e.g., chitosan, may be present in concentrations ranging from about 0 to about 20%, such as from about 2 to about 5% (w/w).

Fillers

Fillers of interest include both reinforcing and non-reinforcing fillers. Reinforcing fillers may be included, such as chopped fibrous silk, polyester, PTFE, NYLON, carbon fibers, polypropylene, polyurethane, glass, etc. Fibers can be modified, e.g., as described above for the other components, as desired, e.g., to increase wettability, mixability, etc. Reinforcing fillers may be present from about 0 to 40%, such as from about 10 to about 30%. Non-reinforcing fillers may also be included, e.g., clay, mica, hydroxyapatite, calcium sulfate, bone chips, etc. Where desired, these fillers may also be modified, e.g., as described above. Non-reinforcing fillers may be present from about 0 to 40%, such as from about 10 to about 30%.

Biologically Active Agents

Biologically active agents may be included, e.g., bone growth factors, tissue activators, cartilage growth activators, small molecule active agents, etc.

Foaming Agent

In certain embodiments, the substrate may include a foaming agent which, upon combination with the crosslinker composition, results in a foaming composition, e.g., a compositions that includes gaseous airbubbles interspersed about. Any convenient foaming agent may be present, where the foaming agent may be an agent that, upon contact with the crosslinking composition, produces a gas that provides bubble generation and, hence, the desired foaming characteristics of the composition. For example, a salt such as sodium bicarbonate in an amount ranging from about 2 to about 5% w/w may be present in the substrate. Upon combination of the substrate with an acidic crosslinker composition, e.g., having a pH of about 5, a foaming composition is produced.

Additional Modifiers

Additional modifiers may also be present. For example, blends of one or more polymers (e.g., polyblends), such as Teflon, PET, NYLON, hydrogels, polypropylene, etc., may be present. The polyblends may be modified, e.g., as described above, to provide for desired properties. These additional modifiers may be present in amounts ranging from about 0 to 50%, including from about 10 to about 30%.

Crosslinker and Preparation Thereof

As indicated above, the phase invertable composition is produced by combining a proteinaceous substrate, as described above, with a crosslinker, where the crosslinker stabilizes the proteinaceous substrate, e.g., by forming covalent bonds between functionalities present on different polypeptide strands of the proteinaceous substrate. Crosslinking typically renders the molecules of the composition less susceptible to chemical degradation, and as such modifies the resorption characteristics of the composition as well as the biological responses induced by the presence of the composition. Numerous crosslinking agents have been identified. Representative examples cross-linkers of interest include, but are not limited to: photo-oxidative molecules; carbodimides; carbonyl containing compounds, e.g., mono- and dicarbonyls, including carboxylic acids, e.g., dicarboxylic acids, such as adipic acid, glutaric acid and the like, and aldehydes, including mono- and dialdehydes, e.g. glutaraldehyde; etc.

In many embodiments, the crosslinker employed is an aldehyde crosslinker. Whereas, any aldehyde crosslinker may be used to crosslink the substrate, glutaraldehyde is employed in many embodiments.

In many embodiments, the aldehyde crosslinker is pre-treated to produce a stabilized aldehyde crosslinker, e.g., a stabilized glutarhaldehyde crosslinker. To produce a stabilized aldehyde, particularly glutaraldehyde crosslinker, an amount of glutaraldehyde is first mixed with water at a particular pH to produce an aqueous glutaraldehyde composition, where the concentration of glutaraldehyde in this composition typically ranges from about 1 to about 20% (w/w), including from about 7 to about 12% (w/w), and the pH ranges from about 5 to about 10, including from about 6 to about 8, e.g., about 7. In producing a stabilized crosslinker, the above initial aqueous glutaraldehyde composition is then heated to a temperature for a period of time sufficient to produce the desired stabilized crosslinker. In this step, the composition maintained at a temperature of from about 35 to about 60° C., such as from about 45 to about 55° C., for a period of time ranging from about 1 to about 20 days, e.g., from about 1 to about 14 days, including from about 72 to about 120 hours. This step may be accomplished via any convenient protocol, e.g., by heating the initial aqueous composition under a nitrogen atmosphere. The product crosslinker is present in a stabilized form. For example, glutaraldehyde heat treated in this manner is present as a complex described by the formula:

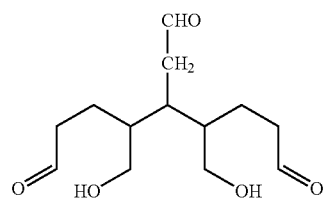

Following heating, the resultant composition is cooled to room temperature and then used as a crosslinker for the proteinaceous substrate. A feature of the heat treated crosslinker is that no additional reducing agents are required to stabilize the crosslinked product upon use, since the heat-treated cross linker, e.g., dialdehyde, is electrovalently in a stable form.

Reaction of the pyridinium precursor complex with the reactive anabilysine, arginine or histidine will result in the structure:

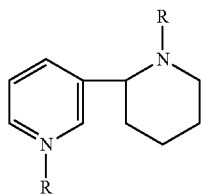

The above structure indicates the ring structures formed upon completion of the pyridinium crosslinks-anabilysine. A more complete understanding of the formation of the stable crosslinks created by anabilysine may be imparted by reviewing the formation of the intermediates, as described in greater detail in U.S. application Ser. No. 10/243,482, the disclosure of which is herein incorporated by reference.

Benefits of using the subject heat treated crosslinkers include the feature that crosslinks produced using heat-treated dialdehydes are covalently bonded structures and are not susceptible to reversal. Thus proteins crosslinked using heat treated glutaraldehyde are more stable and do not exhibit the intense inflammatory responses noted as a result of the reversal of crosslinks when using non-heat treated dialdehydes.

Buffer

Upon mixture of the proteinaceous substrate and crosslinker to produce the subject phase invertable composition, buffering of the phase invertable composition is important for a number of reasons, e.g., to optimize the bonding strength of the composition to the attaching surface, to optimize the conditions necessary for internal crosslinking to occur, etc. For example, optimum crosslinking for proteins using glutaraldehyde crosslinkers occurs at pH range from about 6 to about 8. Buffers capable of maintaining this range are useful in this invention, as long as they do not interfere with the carbonyl terminal of the crosslinker or modify the amine terminus of the amino acids. For example, phosphate buffers have a pKa value in the range of pH 7.0 and do not interfere with the crosslinking process because they do not contain carboxylic or amine functionalities. Phosphate buffer up to 1 M in strength is suitable for use as a buffer in the present invention, where in certain embodiments the phosphate buffer is about 0.2M in strength. While phosphate buffering of the solutions is ideal for the stability of the protein substrate in applications where increased adhesion is required, an acidic buffer may be used as well. Citrate buffers 0.1-1 M and having a pH range of about 4.5 to about 6.5 have been found to be useful for this invention.

The buffer may be present in either the initial crosslinker component or the initial proteinaceous substrate component, or present in both components, as desired.

Combination of Substrate and Crosslinker to Produce Phase Invertable Composition As summarized above, the subject phase invertable compositions are prepared by combining a proteinaceous substrate and crosslinker in appropriate amounts and under conditions sufficient for the phase invertable composition to be produced. The substrate and crosslinker are typically combined in a ratio (v/v) ranging from about 1/5 to about 5/1; so that a resultant phase invertable composition is produced in which the total protein concentration typically ranges from about 10 to about 60%, such as from about 20 to about 50%, including from about 30 to about 40% and the total crosslinker compositions typically ranges from about 0.1 to about 20%, such as from about 0.5 to about 15%, including from about 1 to about 10%.

Combination of the substrate and crosslinker typically occurs under mixing conditions, such that the two components are thoroughly combined or mixed with each other. Combination or mixing may be carried out using any convenient protocol, e.g., by manually combining two components, by employing a device that combines the two components, etc. Combination or mixing is typically carried out at a temperature ranging from about 20 to about 40° C., such as room temperature.

Combination of the proteinaceous substrate and crosslinker as described above results in the production of a phase invertable composition. By phase invertable composition is meant a composition that goes from a first fluid state to a second non-fluid, e.g., gel or solid, state. In the second non-fluid state, the composition is substantially, if not completely, incapable of fluid flow. The phase invertable composition typically remains in a fluid state, following combination of the substrate and crosslinker components, for a period of time ranging from about 10 seconds to about 10 minutes, such as from about 20 seconds to about 5 minutes, including from about 30 seconds to about 120 second, when maintained at a temperature ranging from about 15° C. to about 40° C., such as from about 20° C. to about 30° C.

Methods

The subject biocompatible phase invertable compositions are typically employed in methods where a quantity of the phase invertable composition is delivered to a particular site or location of a subject, patient or host in need thereof. The subject, patient or host is typically a "mammal" or "mammalian," where these terms are used broadly to describe organisms which are within the class mammalian, including, but not limited to, the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the animals or hosts, i.e., subjects (also referred to herein as patients) will be humans.

The quantity that is delivered to the subject in any given application will necessarily vary depending on the nature of the application and use of the composition, but in certain representative embodiments ranges from about 1 to about 50 ml, such as from about 1 to about 25 ml, including from about 1 to about 5 ml, e.g., about 3 ml.

Why necessarily dependent on the particular application in which the subject composition is being employed, the subject composition is, in many embodiments, locally delivered to a particular region, site or location of the host, where the site or location may, of course, vary. Representative sites or locations include, but are not limited to: vessels, organs, and the like. Depending on the particular application, the composition may be delivered to the site of interest manually or with a delivery device, e.g., the delivery device employed to deliver the composition in stenting applications, described in greater detail below.

Utility

The subject biocompatible phase invertable compositions find use in a variety of different applications. Representative applications of the subject phase invertable compositions include those described in U.S. Pat. Nos. 3,438,374; 5,092, 841; 5,292,362; 5,385,606; 5,583,114; 5,843,156; 6,162,241; 6,290,729; 6,302,898; 6,310,036; 6,329,337; 6,371,975; 6,372,229; 6,423,333; 6,458,147; 6,475,182; and 6,547,806;

as well as U.S. Application Nos. 2002/0015724; 2002/0022588; 2002/0133193; 2002/0173770; 2002/0183244; 2002/019490; 2002/0032143; the disclosures of which are herein incorporated by reference.

Representative Vascular Stenting Applications

In one application of particular interest, the subject invention provides methods and devices for producing a biocomposite structural member, e.g., a stent, in situ at a vascular site. In these embodiments, the first step is to position or place a distal end of a fluid composition delivery device at the vascular site where the biocomposite structure member is to be produced. The vascular site in which the structural member is produced in the subject methods is typically a defined location or region of an arterial vessel. By arterial vessel is meant a vessel of a vascularized animal in which blood flows away from the heart. In many embodiments, the arterial vessel is a cardiovascular vessel. In a specific embodiment of interest, the cardiovascular vessel is a coronary artery in which blood flows back into the heart to supply the heart muscle.

In certain embodiments, the fluid composition delivery device is a device that includes at its distal end first and second occlusion members flanking an expandable mandrel. As such, the devices of these embodiments include, at their distal ends, first and second occlusion members separated by an expandable mandrel.

The first and second occlusion members may be any convenient type of occlusion member. In certain embodiments, the occlusion members are deployable balloons, where a variety of balloon occlusion members are known in the relevant art and may be employed in the subject devices. In yet other embodiments, the occlusion members are non-balloon occlusion members, such as occlusion members that, upon deployment, produce a collar configuration that results in blockage of fluid flow in the vessel at the location of deployment. The above described occlusion members are merely representative of the types of occlusion members that may be employed, where the only requirement is that the member serve to occlude the vessel at the region of deployment, i.e., that the member substantially, if not completely, stop the flow of blood into and out of the region that is occluded.

Positioned between the first and second occlusion members is an expandable mandrel. As such, an expandable structure around which a phase invertable fluid may be placed and allowed to set, as described below, is present between the first and second occlusion members. The expandable mandrel, in many embodiments, includes one or more fluid introduction and removal ports, where these ports are holes or analogous structures that serve as entry or exit paths for fluid to enter or leave fluid conveyance structures, e.g., lumens, that lead from the distal end of the device to a different location of the device, e.g., to the proximal end of the device, for example a fluid reservoir in fluid communication with the proximal end of the device.

A feature of certain (though not all) embodiments is that the expandable mandrel expands or deploys as a function of either deployment of the first and second occlusion members or initiation of delivery of a phase invertable fluid composition to the vascular site of interest. As such, in certain embodiments the device is one in which deployment of the first and second occlusion members results in deployment of the expandable mandrel. In yet other embodiments, deployment of the expandable mandrel occurs as a function of introduction of the phase invertable fluid composition to the vascular site, e.g., upon introduction of fluid into a delivery lumen of the device.

Following placement or positioning of the distal end of the device, as described above, at the vascular site, the first and second occlusion members and expandable mandrel are deployed to produce a mold space for the structural member to be formed in situ at the vascular site. The produced mold space is bounded at either end by the first and second occlusion members. The lumen of the vessel in which the vascular site is located serves as the outer wall of the mold space and the expandable mandrel serves as the inner wall of the mold space. As such, the mold space defines a tubular volume of space bounded in the inner surface by the mandrel, on the outer surface by the lumen of vessel at the vascular site, and at the top and bottom by the first and second occlusion members.

In the subject methods, a phase invertable fluid composition is then introduced into the mold space, as defined above. While in the broadest sense, the phase invertable fluid composition may be any fluid that is capable of phase inverting from a first fluid composition to a second solid composition over a period of time into a physiologically acceptable biocomposite structural member, e.g., a stent, in many embodiments the phase invertable material employed is the phase invertable material of the present invention, as described above. In those embodiments where the phase invertable fluid composition is one that is prepared from a substrate and a cross-linker, e.g., such as the representative composition described above, the device employed in the subject methods may have elements for mixing or combining the substrate and crosslinker at the vascular site (for example at the point where the fluid exits a port in the mandrel), or at a position upstream of the vascular site, e.g., at a location at the proximal end of the fluid delivery device.

Following introduction of the phase invertable material, the phase invertable fluid composition now present in the mold space is allowed to undergo a phase inversion to said second solid state. Next, the expandable mandrel and occlusion members are retracted or collapsed, and the distal end of the device is removed from the vascular site, leaving the resultant biocomposite structural member at the vascular site. As such, practice of the subject methods results in the in situ production of a biocomposite structural member at a vascular site.

Specific Representative Embodiments

FIGS. 1A to 1E provide an illustration of the practice of a representative method according to the subject method where a biocomposite stent is produced in situ at a vascular site having a stenotic lesion on a luminal surface of an arterial vessel.

FIG. 1A provides a cross-sectional view of a coronary artery 10 showing vessel walls 12 and stenotic lesion 14 present on the luminal surface thereof.

Figure 1B:
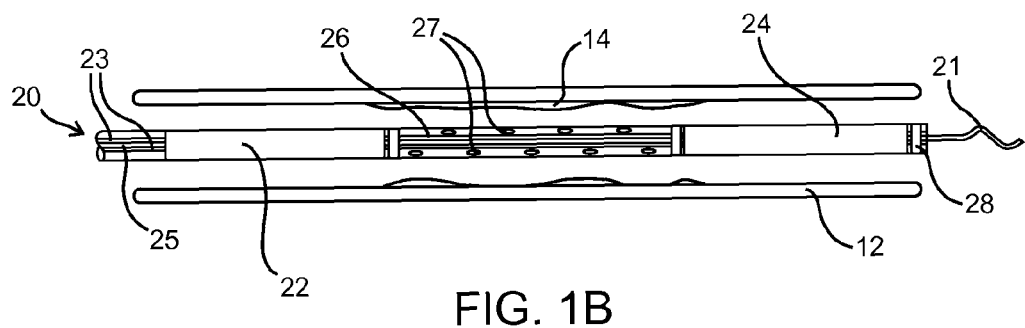

FIG. 1B shows placement of device 20 at the vascular site occupied by the lesion 14, where the lesion has been compacted against the luminal surface of the vessel, e.g., using standard balloon angioplasty techniques. Device 20 is a catheter device having a proximal occlusion balloon 22 and a distal occlusion balloon 24 flanking, i.e., separated by, an expandable mandrel 26. Adjacent the distal occlusion balloon 24 is marker band 28. Also shown is guidewire 21. Guidewire 21 and marker band 28 to aid in placement of the distal end of the device at the vascular site. Balloon lumens 23 are also shown, as is a fluid delivery lumen 25. Present on the surface of expandable mandrel 26 are a plurality of fluid entry and exit ports 27, which are used to introduce fluid into and/or remove fluid from a mold space produced upon deployment of the occlusion members and expandable mandrel.

Figure 1C:
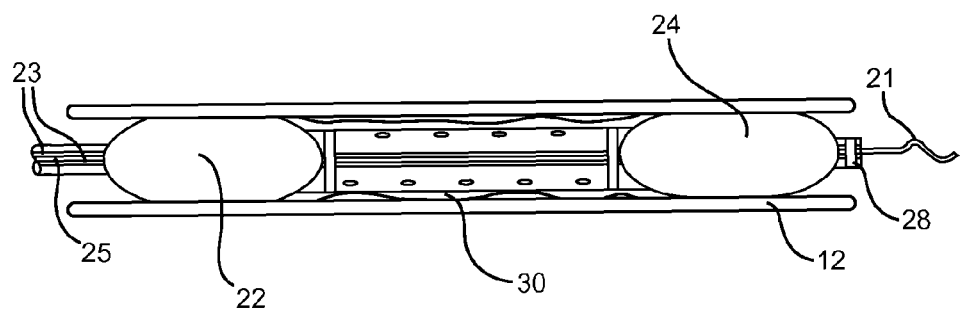

In FIG. 1C, the proximal and distal balloons and the expandable mandrel have been deployed to produce a stent mold space 30 at the vascular site, where the stent mold 30 is a tubular volume that is bounded at either end by the distal and proximal occlusion balloons, on the outer surface by the lumen having the compressed lesion thereon, and on the inner surface by the expandable mandrel.

Figure 1D:
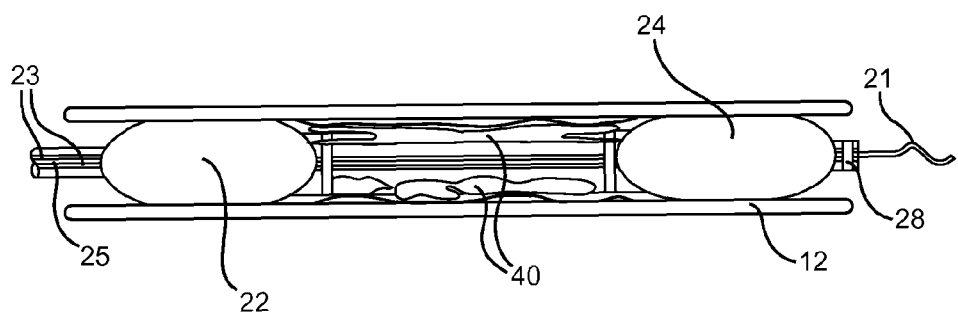

FIG. 1D shows introduction of phase invertable material 40 into the mold space 30, e.g., via ports 27.

Figure 1E:
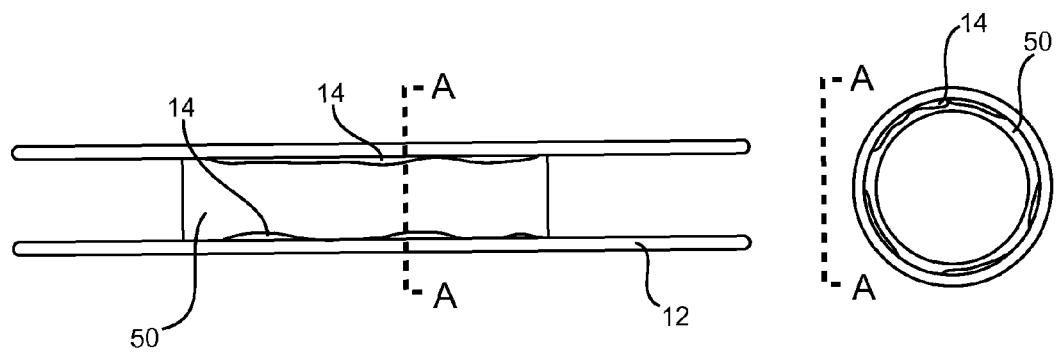

The introduced phase invertable fluid composition is then allowed to set or harden, following which device 20 is removed from the vascular site, leaving behind a biocomposite stent 50 depicted in FIG. 1E.

Figure 2:
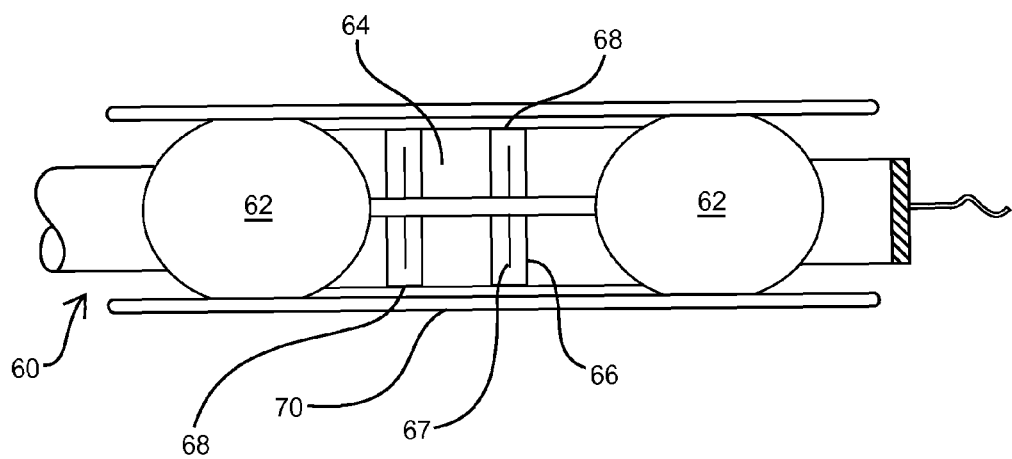
FIG. 2 provides a representation of an alternative embodiment of a delivery device according to the subject invention.

An alternative embodiment of a delivery device according to the present invention is shown in FIG. 2. In FIG. 2, delivery device 60 is shown in a deployed configuration at a location in vessel 70. Balloons 62 and mandrel 64 are deployed, and present in mandrel 64 are multiple delivery tubes 66 which convey the two component parts of a phase invertable composition, i.e., a substrate and linker (as described below) from separate fluid delivery lumens in device 60 to exit ports 68. At the distal end of each delivery tube 66 is a mixing element 67 which assists in combining the two component parts immediately prior to exit from the device.

In yet another alternative embodiment, the expandable mandrel has multiple delivery tubes via which individual components of the two-part phase invertable composition, i.e., the substrate and linker compositions, are delivered through separate exit ports. After delivery of substrate material to the lesion site, the linker composition is delivered to the site with simultaneous pulsation (i.e. inflation and deflation) of the expandable mandrel for the purpose of mixing the two components.

In yet another alternative embodiment, the substrate material is deployed as a solid matrix on the exterior of the expandable mandrel and then expanded to the wall of the vessel in a tubular form by expansion of the mandrel. Once in position, the linker composition is delivered through the expandable mandrel and allowed to come in contact with, and mix with, the previously deployed substrate material.

The subject methods and devices of these particular representative embodiments, as described above, find use in any application where the production of a biocomposite structural member in situ at a vascular site is desired. One representative type of application in which the subject methods find use is in the production of a biocomposite stent at a stenotic vascular site, e.g., a coronary artery, where the lesion has been treated, e.g., compressed, via atherectomy or angioplastic techniques, to increase the flow of blood through the artery.

Generally the vascularized animals with which the subject invention is employed are "mammals" or "mammalian," where these terms are used broadly to describe organisms which are within the class mammalian, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the animals or hosts, i.e., subjects (also referred to herein as patients) will be humans.

Also provided are systems for use in practicing the subject methods of this embodiment, where the systems at least include a fluid delivery device and a phase invertable fluid composition, as described above. The subject systems also typically include a guiding element that is employed to position the device, e.g., in a percutaneous approach protocol, such as a guidewire or analogous structure. Other components that may be present in the subject systems include, but are not limited to: balloon inflation means, etc.

Kits

Also provided are kits for use in practicing the subject methods, where the kits typically include a distinct substrate and crosslinker components of a phase invertable fluid composition, as described above. The substrate and crosslinker components may be present in separate containers in the kit, e.g., where the substrate is present in a first container and the crosslinker is present in a second container, where the containers may or may not be present in a combined configuration.

The subject kits may also include a mixing device, for mixing the substrate and crosslinker together to produce the phase invertable composition. The kits may also include a delivery device (which may or may not include a mixing element), such as a catheter devices, as described above.

The kit may further include other components, e.g., guidewires, sensor wires, etc., which may find use in practicing the subject methods.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are provided by way of illustration and not by way of limitation.

EXPERIMENTAL

I. Functionality of Heat Treated Glutaraldehyde

Heat-treated glutaraldehyde was evaluated to determine crosslinking efficiency. Glutaraldehyde solution (5% w/w) was used to crosslink a solution containing 35% albumin. The albumin was polymerized in approximately 90 seconds, indicating the efficiency of the crosslinking solution of the glutaraldehyde was undisturbed.

II. Representative Uses

A. Pulmonary

A rabbit was used and an experimental model for the evaluation of the material as a pulmonary sealant.

A sealant composition of the subject invention, consisting of albumin, collagen, oleic acid, PEI and chitosan and crosslinked with heat-processed glutaraldehyde, was prepared in accordance with the method of invention. Concentrations for each ingredient were consistent with the values indicated in the above examples.

The lungs of an anaesthetized rabbit were exposed and deflated. Following, a portion of the upper lobe of the lung was transected and the cut site of the deflated lung was sealed and reinflated. The lung was evaluated for leakage by submersion in water. Evaluation of the lung for air leakage did not indicate any to be present, indicating the efficacy of the sealant.

B. Vascular

A rabbit was again used as an experimental model for the evaluation of the material as a vascular sealant.

In this experiment, the carotid arteries of an anesthetized, anticoagulated rabbit were bilaterally exposed. The artery of the left side was punctured with a 14 F catheter. Following removal of the catheter the hole was closed using the sealant. Alternately, the artery of the right side was transected, and an anastomosis was created using 6-0 Prolene suture. An umbilical tape was partially looped around the vessel proximal to the surgery site to momentarily reduce blood flow.

Sealant formulated to be consistent with the ranges heretofore indicated was applied to the puncture site using a tipped syringe. Following three minutes, the pressure was released to expose the repair to the full systolic/diastolic pressure of the carotid artery. No leakage was found to be present from the wound site.

Sealant formulated to be consistent with the ranges indicated was applied to the partially leaking anastomotic site of the right side of the experimental model. Following three minutes it was noted that the leakage stopped.

C. Cerebral Spinal Fluid

In a further experiment, a human cadaveric model was assessed for adhesion of the sealant onto the dura mata.

Following a craniotomy, the exposed dura was incised. Incision of the dura resulted in retraction of the tissue. The retracted tissue was drawn together, again using temporary stay sutures such that the incised edges were juxtaposed to one another. Sealant consistent with the formulations noted for this invention was prepared. The sealant was applied over the incision wound and the suture stays were released. The opposing edges of the incision wound remained aligned with one another, the sealant demonstrating adequate tenacity to resist the retractive forces of the dura. The cadaver's head was lowered placing additional stress on the suture and the site was observed for failure of the sealant to hold the edges together. No failures were noted.

III. Tissue Compatibility Testing

A sealant composition of the subject invention, consisting of albumin, collagen, oleic acid, PEI and chitosan and crosslinked with heat-processed glutaraldehyde, was prepared in accordance with the method of invention. Concentrations for each ingredient were consistent with the values indicated in the above examples.

The composition was implanted in muscle tissue of a living rabbit. The muscle tissue was then evaluated for evidence of irritation or toxicity based on the requirements of the International Organization for Standardization 10993: Biological Evaluation of Medical Devices, Part 6: Tests for Local Effects after Implantation.

Implant samples and negative control samples were sterilized by ethylene oxide and then degassed for 5 days. Rabbits were implanted and were then euthanized 3 weeks later. Muscle tissues were excised and the implant sites were examined macroscopically. A microscopic evaluation of representative implant sites from each rabbit was conducted to further device any tissue response.

Under the conditions of this study, the macroscopic reaction was not significant as compared to the negative control implant material. Microscopically, the test article was classified as a non-irritant as compared to the negative control article.

It is evident from the above results and discussion that the present invention provides an important new type of biocompatible composition that can be used in a variety of different applications, where benefits of the subject compositions include, but are not limited to, low toxicity, high adhesion, and the like. Accordingly, the present invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of producing a phase invertable composition, said method comprising:
   combining:
   (a) a substrate comprising a proteinaceous material; and
   (b) a heat-stabilized aldehyde crosslinking agent that has been produced by maintaining an initial aldehyde crosslinking composition at an elevated temperature that ranges from about 45 to about 55° C. for a period of time that ranges from about 1 to about 20 days;
   to produce said phase invertable composition.

2. The method according to claim 1, wherein said proteinaceous material comprises one or more of: albumin, elastin, fibrin and soluble and insoluble forms of collagen and combinations thereof.

3. The method according to claim 1, wherein said substrate further comprises an adhesion modifier.

4. The method according to claim 3, wherein said adhesion modifier is chosen from polyethyleneimine, gelatin and carboxymethylcellulose.

5. The method according to claim 1, wherein said substrate further comprises a plasticizer.

6. The method according to claim 5, wherein the plasticizer is chosen from polyethylene glycol, glycerin, a fatty acid, butylhydroxytoluene, and combinations thereof.

7. The method according to claim 1, wherein said substrate further comprises a carbohydrate.

8. The method according to claim 1, wherein said substrate further comprises a filler.

9. The method according to claim 1, wherein said substrate further comprises a polyblend of one or more modifying polymers.

10. The method according to claim 1, wherein said substrate further comprises a biologically active agent.

11. The method according to claim 1, wherein said substrate further comprises a foaming agent.

12. The method according to claim 1, wherein said heat-stabilized aldehyde crosslinking agent comprises heat-stabilized glutaraldehyde.

13. A method of placing a biocompatible composition to a site of a subject, said method comprising:
  (a) preparing a phase invertable composition by combining:
    (i) a substrate comprising a proteinaceous material; and
    (ii) a heat-stabilized aldehyde crosslinking agent that has been produced by maintaining an initial dialdehyde crosslinking composition at an elevated temperature that ranges from about 45 to about 55° C. for a period of time that ranges from about 1 to about 20 days;
  to produce said phase invertable composition; and
  (b) introducing said phase invertable composition to said site of said subject.

14. The method according to claim 13, wherein said phase invertable composition is prepared at a site external to said subject.

15. The method according to claim 13, wherein said phase invertable composition is prepared at said site.

16. A kit for producing a phase invertable composition, said kit comprising:
  (a) a substrate comprising a proteinaceous material;
  (b) a heat-stabilized aldehyde crosslinking agent that has been produced by maintaining an initial dialdehyde crosslinking composition at an elevated temperature that ranges from about 45 to about 55° C. for a period of time that ranges from about 1 to about 20 days.

17. The kit according to claim 16, wherein said kit further comprises a phase invertable fluid delivery device.

18. The method according to claim 1, wherein the heat stabilized aldehyde crosslinking agent comprises a heat stabilized dialdehyde.

19. A method of producing a phase invertible composition, said method comprising:
  combining:
    (a) a substrate comprising a proteinaceous material; and
    (b) a heat-stabilized aldehyde crosslinking agent that produces pyridinium crosslinks of proteins of the proteinaceous material;
  to produce said phase invertable composition.

20. The method according to claim 19, wherein the heat stabilized aldehyde crosslinking agent comprises a heat stabilized dialdehyde.

21. The method according to claim 19, wherein said heat-stabilized aldehyde crosslinking agent comprises heat-stabilized glutaraldehyde.

* * * * *